United States Patent [19]

Fullerton

[11] 4,199,565

[45] Apr. 22, 1980

[54] LIPOSOME PARTICLE CONTAINING VIRAL OR BACTERIAL ANTIGENIC SUBUNIT

[75] Inventor: William W. Fullerton, King of Prussia, Pa.

[73] Assignee: Merck & Co., Inc., Rahway, N.J.

[21] Appl. No.: 24,144

[22] Filed: Mar. 26, 1979

[51] Int. Cl.$^2$ ................... A61K 39/12; A61K 39/02; A61K 39/18
[52] U.S. Cl. ........................................ 424/89; 424/88; 424/92
[58] Field of Search .................................. 424/88–92

[56] References Cited

U.S. PATENT DOCUMENTS

| | | | |
|---|---|---|---|
| 4,053,585 | 10/1977 | Allison et al. | 424/92 |
| 4,117,113 | 9/1978 | Allison et al. | 424/89 |
| 4,148,876 | 4/1979 | Almeida et al. | 424/89 |

FOREIGN PATENT DOCUMENTS 2643641  4/1977  Fed. Rep. of Germany .

OTHER PUBLICATIONS

Chem. Abstracts 89 #157972d, #1994b 88 #1961t #20444t #35717h (1978); 87 #50741j #11609c #130406u (1977).
Allison et al., Nature 252, Nov. 15, 1974: 252 "Liposomes as Immunological Adjuvants".
Manesis et al., Biochem Soc. Trans. 6(5) 925–928 (1978), Incorporation of Heptatis–B Surface Antigen (HBsAG) Into Liposomes.
Van Rooijen et al., Immunol. Commun. 1977 6(5) 489–498 7(6) 635–644 (1978), Liposomes in Immunology: The Immune Response Against Antigen–Containing Liposomes; Further Evidence for the Adjuvant Activity of Liposomes.
Morein et al., Nature 276 (5689), 715–718, Dec. 14, 1978, Effective Subunit Vaccines Against an Enveloped Virus.
Almeida et al., Lancet, Nov. 8, 1975, 899–901, Formation of Virosomes from Influenza Subunits and Liposomes.

*Primary Examiner*—Shep K. Rose
*Attorney, Agent, or Firm*—Donald J. Perrella; Julian S. Levitt

[57] ABSTRACT

Subunit viral or bacterial antigens are incorporated into liposomes containing a positively charged amino-containing surfactant. The resulting complex is antigenically more active than the free antigen.

5 Claims, No Drawings

LIPOSOME PARTICLE CONTAINING VIRAL OR BACTERIAL ANTIGENIC SUBUNIT

BACKGROUND OF THE INVENTION

Attempts to reduce the side effects often encountered in administration of a vaccine have led to the use of a subunit antigen. Such subunit, however, is usually much less immunogenic than the whole intact antigenin starting material.

OBJECTS OF THE INVENTION

It is an object of the present invention to increase the antigenicity of a subunit antigenic preparation. A further object is to provide a particle wherein the subunit is attached to a liposome. Still another object is to provide a method for preparing such a particle. These and other objects of the present invention will be apparent from the following description.

SUMMARY OF THE INVENTION

A subunit viral or bacterial antigen is incorporated into a lipid which contains a positively charged amino-containing surfactant, or the subunit antigen is reacted with a positively charged amino-containing surfactant to form a complex which is incorporated into a lipid.

DETAILED DESCRIPTION

The present invention relates to an antigenic subunit vaccine and, more particularly, to an antigenic subunit vaccine incorporated into a liposome. A liposome is a continuous lipid surface, either unilamellar or multilamellar, enclosing a three-dimensional space.

It has been found according to the present invention that an antigenic subunit may be incorporated into a lipid containing a positively charged amino-containing surfactant and that an antigenic subunit may be reacted with a positively charged amino-containing surfactant and the resulting complex incorporated into a lipid.

The liposome is prepared from either a natural or synthetic phosphocholine-containing lipid having either two fatty acid chains of from 12 to 20 carbon atoms, or one fatty acid chain of from 12 to 20 carbon atoms and a second chain of at least 8 carbon atoms. In general, synthetic lipids are preferred as they have fewer impurities. The synthetic lipid may be a phosphatidylcholine containing two fatty acid side chains from 12 to 20 carbon atoms. Some suitable synthetic lipids are, for example dimyristoylphosphatidylcholine,
dioleoylphosphatidylcholine,
dipalmitoylphosphatidylcholine, and
distearoylphosphatidylcholine, while some suitable natural lipids are, for example:
phosphatidylcholine, and
sphingomyelin.

The positively charged amino-containing surfactant may be a fatty acid amine of from 12 to 20 carbon atoms such as, for example, cetylamine and stearylamine, or a salt of an amino-containing surfactant such as, for example, cetyl benzyldimethyl ammonium chloride,
N-hexadecylpyridinium chloride,
hexadecyltrimethyl ammonium bromide, and
cetyltrimethyl ammonium bromide.

The antigen which is incorporated into a liposome containing a positively charged amino-containing surfactant or which is complexed with such a surfactant and then incorporated into a liposome is prepared according to techniques known to be effective to produce protein or glycoprotein subunits, or a mixture of protein and glycoprotein subunits. Antigenic subunits may be prepared from many types of virus such as, for example, influenza types A and B, herpes 1 and herpes 2, hepatitis A and hepatitis B. It is also possible to incorporate gram negative bacteria subunits into a lipid according to the methods of the present invention, e.g., protein and/or glycoprotein from bacteria such as, for example, N. gonorrhoeae and complex polysaccharides such as, for example, those from Meningococcus A and C. In the case of influenza virus, the antigenic subunit may be prepared by extraction of the virus with a nonionic surfactant, e.g. Triton X-100, followed by precipitation with a material in which the extract is insoluble, e.g., n-butanol, and washing with ether followed by dialysis against either deionized distilled water or phosphate buffered saline (PBS), pH 7.2, at 2°–4°.

According to a first technique for preparing the subunit viral liposome particle of the present invention, the positively charged amino-containing surfactant and the phospholipid are dried together. The subunit virus or bacterial antigens in aqueous medium (water or low molarity buffer, pH 6.8–7.4), is then added under liposome forming conditions, such as agitation, e.g., bath sonication for from about 2 to about 8 minutes, whereby the subunit viral antigens are incorporated into the liposome containing a positively charged amino-containing surfactant.

In a second technique the subunit virus or bacterial antigens are reacted directly with the positively charged amino-containing surfactant. This, as an aqueous (water only) suspension, is then added to the dry phospholipid and the preparation agitated, e.g., by bath sonication for from about 2 to about 8 minutes.

The following examples illustrate the present invention without, however, limiting the same thereto. All temperatures are expressed in degrees Celsius.

EXAMPLE 1

Dioleoylphosphatidylcholine (20 mg in 0.8 ml chloroform) and stearylamine (3 mg dry powder dissolved in 1–2 ml dry chloroform) are mixed together at room temperature for 1–2 minutes in a 50 ml round bottom or pear-shaped flask and then dried down rapidly in vacuo at 37°. Immediately after drying, pure dry nitrogen gas is blown into the flask for 2–3 minutes. The influenza A victoria subunit antigen at 750 μg hemagglutinin (HA) units/ml in 3.5 ml of deionized distilled water or phosphate buffered saline (pH 7.2) is added slowly. Nitrogen gas is continuously, slowly bubbled through the solution which is placed in the center of a small (13.5 cm × 13.5 cm) ultrasonic cleaner bath (Cole-Parmer) filled 6 cm 8 cm deep with water which contains 1 ml of Triton X-100 as detergent to lower the surface tension. The cleaner bath operates at 50–55 KHz and is maintained at 20°–25° by addition of ice. The solution is sonicated, with occasional swirling of the contents, for 2–8 minutes, typically for 7 minutes. After sonication the contents of the flask are transferred to a 6 ml serum bottle and capped with a rubber stopper. The sonicated material is stored at 2°–4°.

EXAMPLE 2

Stearylamine (3 mg) plus ethanol (0.4 ml) are heated to 55°–60° for 1–2 minutes until the stearylamine is completely soluble. Then deionized, distilled water (2.6 ml) which has been heated to 55°–60° is slowly added with swirling. At this stage the solution may be opalescent, but there should be no precipitate. Pure, dry nitrogen gas is bubbled through the solution for 5–10 minutes, typically 8 minutes, until the solution is cooled to 30°–40°. Then the influenza A Victoria subunit antigen at 750 μg hemagglutinin (HA) units per ml at 25°–30° in 0.9 ml deionized, distilled water is slowly added and nitrogen gas bubbled through for a further 2–6 minutes, typically 4 minutes. No obvious precipitate should be present. Next, the antigenstearylamine preparation is slowly added to a dried down preparation of dioleoylphosphatidylcholine (20 mg) in a 50 ml round bottom glass flask. The solution is sonicated for 2–8 minutes, typically for 7 minutes, in a Cole-Parmer ultrasonic cleaner bath at 50–55 KHz while continuously bubbling nitrogen gas therethrough. The temperature of the cleaner bath is maintained at 20°–25° by the addition of ice. During sonication the contents of the flask are occasionally swirled. After sonication the contents of the flask are transferred to a 6 ml serum bottle, capped with a rubber stopper, and stored at 2°–4°.

EXAMPLE 3

Stearylamine (3.008 mg) plus anhydrous chloroform (2 ml) plus dioleoylphosphitidylcholine (20.0 mg in 0.8 ml chloroform) are mixed together at room temperature in a 50 ml pear-shaped glass flask along with 2 ml dry chloroform in transfer washings. After drying in vacuo at 30° on a rotary evaporator, pure dry nitrogen gas is blown in at room temperature for 2 minutes. Hepatitis B subunit vaccine material (40 μg/ml protein, 5 ml in 0.063 M sodium phosphate buffer, pH 7.0) is slowly added and the preparation sonicated for 7 minutes at room temperature in an ultrasonic cleaner bath (50–55 KHz) with nitrogen gas bubbling through the solution. After sonication the contents of the flask are transferred to a 6 ml serum bottle, capped with a rubber stopper, and stored at 2°4°.

EXAMPLE 4

Liposomes and Triton-Butanol Subunit HA from Influenza Type A Virus

| 6.25 HA units per 0.25 ml dose | Arithmetic mean hemagglutination Inhibition Titer after 21 Days in Mice |
|---|---|
| Whole live Influenza Type A | 53 |

EXAMPLE 4-continued

Liposomes and Triton-Butanol Subunit HA from Influenza Type A Virus

| 6.25 HA units per 0.25 ml dose | Arithmetic mean hemagglutination Inhibition Titer after 21 Days in Mice |
|---|---|
| Formalin killed Influenza Type A | <10 |
| Subunit Influenza Type A (HA) | <10 |
| (S + DOPC) + (HA) | 40 |
| (S + DSPC) + (HA) | 20 |
| (S + HA) + DOPC | 33 |
| (S + HA) + DSPC | <10 |
| DOPC + HA | <10 |
| DSPC + HA | <10 |

S = stearylamine
DOPC = dioleoylphosphatidylcholine
DSPC = distearoylphosphatidylcholine

EXAMPLE 5

Liposomes and Hepatitis B subunit

| Test Group | Antibody Conversions (antibody positive/total mice) |
|---|---|
| (S + DOPC) + RCM7 | 0/20 |
| Hepatitis B subunit | 2/20 |
| (S + DOPC) + Hepatitis B subunit | 8/20 |
| Alum + Hepatitis B subunit | 13/20 |

S = stearylamine
DOPC = dioleoylphosphatidylcholine
RCM7 = 0.063 M phosphate buffer (pH 7.0)

Experiment

Five-week old ICR mice (20 per group) are given a single subcutaneous injection of 1.25 μg of hepatitis B subunit material (40 μg/ml protein). On day 42, the mice are bled and the sera subsequently individually assayed (Ausab) for anti-$HB_3Ag$ antibody.

What is claimed is:

1. A particle comprising a liposome containing a fatty acid amine of from 12 to 20 carbon atoms as a positively charged amino-containing surfactant reacted with a viral or bacterial subunit antigen.

2. A particle according to claim 1 wherein the positively charged amino-containing surfactant and the subunit antigen are present as a complex.

3. A particle according to claim 1 wherein the positively charged amino-containing surfactant and the lipid are present as a complex.

4. A particle according to claim 1 wherein the liposome is formed from a phosphatidylcholine-containing lipid.

5. A particle according to claim 1 wherein the subunit antigen is derived from influenza virus, hepatitis B virus, *N. gonorrhoeae,* or Meningococcus polysaccharide types A or C.

* * * * *